(12) United States Patent
Esashi et al.

(10) Patent No.: US 10,190,122 B2
(45) Date of Patent: *Jan. 29, 2019

(54) INHIBITORY OLIGONUCLEOTIDE AND USE THEREOF

(71) Applicant: SBI Biotech Co., Ltd., Tokyo (JP)

(72) Inventors: Eiji Esashi, Tokyo (JP); Liying Wang, Changchun (CN); Yongli Yu, Changchun (CN)

(73) Assignee: SBI Biotech Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/605,488

(22) Filed: May 25, 2017

(65) Prior Publication Data
US 2017/0335325 A1 Nov. 23, 2017

Related U.S. Application Data

(63) Continuation of application No. 14/442,799, filed as application No. PCT/CN2012/085547 on Nov. 29, 2012, now Pat. No. 9,688,992.

(51) Int. Cl.
*A61K 31/711* (2006.01)
*C12N 15/117* (2010.01)
*A61K 47/61* (2017.01)

(52) U.S. Cl.
CPC .......... *C12N 15/117* (2013.01); *A61K 31/711* (2013.01); *A61K 47/61* (2017.08); *C12N 2310/17* (2013.01); *C12N 2310/315* (2013.01); *C12N 2310/351* (2013.01); *C12N 2320/30* (2013.01); *C12N 2320/31* (2013.01)

(58) Field of Classification Search
CPC . C12N 15/113; C12N 2310/14; A61K 31/713
USPC ........... 435/6.1, 91.1, 91.31, 455, 458, 6.11; 514/44; 536/23.1, 24.5
See application file for complete search history.

(56) References Cited

U.S. PATENT DOCUMENTS

| 8,030,289 B2 | 10/2011 | Wang et al. |
| 2010/0035972 A1 | 2/2010 | Wang et al. |
| 2013/0323242 A1* | 12/2013 | Everett .............. A61K 39/3955 424/134.1 |
| 2015/0299710 A1 | 10/2015 | Esahi et al. |

FOREIGN PATENT DOCUMENTS

| CN | 101240271 | 8/2008 |
| CN | 102612561 | 7/2012 |
| CN | 102851295 | 1/2015 |
| WO | 2005/072290 | 8/2005 |
| WO | 2010/015148 | 2/2010 |

OTHER PUBLICATIONS

Hu et al, Molecular Immunology, vol. 46, pp. 1387-1396 (2009).*
Sun et al, Clinical Immunology, vol. 134, pp. 262-276 (2010).*
Baldwin (Jr) AS, et al., "The NFκ-B and IκB Proteins: New Discoveries and Insights," Annu Rev Immunol. 1996, 649-683.
Barrat FJ, et al., "Nucleic acids of mammalian origin can act as endogenous ligands for Toll-like receptors and may promote systemic lupus erythematosus," J Exp Med 2005; 202: 1131-9.
Boule MW, et al., "Toll-like Receptor 9-Dependent and-Independent Dendritic Cell Activation by Chromatin-Immunoglobulin G Complexes," J Exp Med 2004; 199:1631-40.
Christensen SR, et al., "Toll-like Receptor 7 and TLR9 Dictate Autoantibody Specificity and Have Opposing Inflammatory and Regulatory Roles in a Murine Model of Lupus," Immunity 2006; 25:417-28.
Espat NJ, et al., "PEG-BP-30 Monotherapy Attenuates the Cytokine-Mediated Inflammatory Cascade in Baboon *Escherichia coli* Septic Shock," J Surg Res. Jul. 1995; 59 (1):153-8.
Fang M., et al., "An oligodeoxynucleotide capable oflessening acute lung inflammatory injury in mice infected by influenza virus," Biochem. Biophys. Res. Comm. 2011; 415: 342-347.
Foo Y. et al., "Negative regulation of Toll-like receptor-mediated immune responses," Nature Review Immunology, vol. 5, 2005, 446-458.
Gilliet M, et al., "Plasmacytoid dendritic cells: sensing nucleic acids in viral infection and autoimmune diseases," Nat. Rev. Immunol. 2008, 594-606.
Goldsby, Richard A et al. Immunology, Fifth Edition, 2003, W.H. Freeman and Company,# Regarding 'Graft Rejection', please refer pp. 480-485 and 488-489; #Regarding 'Hypersensitive Reactions', please mainly refer p. 362.
Haizhen, Research progress of immune inhibitory oligonucleotides (ODN), Guide of China Medicine, Jan. 31, 2011(Jan. 31, 2011), vol. 9, No. 18, pp. 225-226, ISSN: 1671-8194.
He C., et al., "Effects of oligodeoxynucleotide with CCT repeats on chronic graft versus host disease induced experimental lupus nephritis in mice," Clin Immunol. 2011; 140:300-306.
Hu D., et al., "Human microsatellite DNA mimicking oligodeoxynucleotides down-regulate TLR9-dependent and -independent activation of human immune cells," Molecular Immunol. 2009; 46, 1387-1396.
International Search Report for PCT/CN2012/085547 dated Aug. 8, 2013.
Klinman, D.M., "Immunotherapeutic uses of CpG oligodeoxynucleotides," Nat. Rev., Immunol. 4 (2004) 249-258.
Krieg, A.M., "Therapeutic potential of Toll-like receptor 9 activation," Nature Reviews Drug Discovery, vol. 5. Jun. 2006, 471-484.
Kwok SK, et al., "A high serum level of eotaxin (CCL 11) is associated with less radiographic progression in early rheumatoid arthritis patients," Arthritis Res Ther. 2008;10(2):R29.
Leadbetter EA, et al., "Chromatin-IgG complexes activate B cells by dual engagement oflgM and Toll-like receptors," Nature 2002; 416:603-7.

(Continued)

*Primary Examiner* — Jane J Zara
(74) *Attorney, Agent, or Firm* — Fish & Richardson P.C.

(57) ABSTRACT

The inhibitory oligonucleotides (ODNs) strongly block NF-κB activation induced by TLR9 agonists and TLR7 agonists. The production of proinflammatory cytokines, such as interleukin-6 and tumor necrosis factor alpha, is inhibited by the inhibitory-ODNs. Interferon production from human PBMC induced by TLR9 agonist is prevented by the inhibitory-ODNs. These ODNs can be used as a remedy for the treatment of immune-mediated disorders such as rheumatoid arthritis, systemic lupus erythematosus (SLE), sepsis, multiple organ dysfunction syndromes.

18 Claims, 9 Drawing Sheets
Specification includes a Sequence Listing.

(56) References Cited

OTHER PUBLICATIONS

Marshall AJ, et al., "Toxoplasma gondii Triggers Granulocyte-Dependent Cytokine-Mediated Lethal Shock in D-Galactosamine-Sensitized Mice," Infect Immun. Apr. 1998, 66(4): 1325-33.

Miyazawa K, et al., "Constitutive Transcription of the Human Interleukin-6 Gene by Rheumatoid Synoviocytes Spontaneous Activation of NF-KB and CBF1," Am J Pathol 1998, 793-803.

Muraiso T., et al., "A single-stranded DNA binding protein from mouse tumor cells specifically recognizes the Crich strand of the (AGG:CCT)n repeats that can alter DNA conformation," Nuc Acids Res. 1992; 20(24): 6631-6635.

Neurath MF, et al., "Cytokine Gene Transcription by NF-KB Family Members in Patients with Inflammatory Bowel Disease," Ann Ny Acad Sci 1998, 859:149-159.

Peter M, et al., "Characterization of suppressive oligodeoxynucleotides that inhibit Toll-like receptor-9-mediated activation of innate immunity," Immunology. Jan. 2008; 123(1):118-28.

Schottelius AJ, et al., "Interleukin-10 Signaling Blocks Inhibitor of kB Kinase Activity and Nuclear Factor kB DNA Binding," J Biol Chem 1999, 31868-31874.

Slifka MK, et al., "Clinical implications of dysregulated cytokine production," J Mol Med. 2000; 78(2):74-80.

Sun Ran, Inhibitory effect of oligonucleotides containing CCT on TLR7 /9 mediated innate immune response, China Doctor Dissertation Full-text Database, Aug. 4, 2009 (Aug. 4, 2009), ISSN: 1674-022X.

Sun, R, et al., A human microsatellite DNA-mimicking oligodeoxynucleotide with CCT repeats negatively regulates TLR7 /9-mediated innate immune responses via selected TLR pathways, Clinical Immunology, Jan. 19, 2010 (Jan. 19, 2010), vol. 134, pp. 262-276, ISSN:0271-9142.

The Writing Committee of the World Health Organization (WHO) Consultation on Human Influenza A/HS. Avian Influenza A (H5N1) Infection in Humans. N Engl J Med 2005; 353: 1374-85.

Wang H, et al. "The cytokine storm and factors determining the sequence and severity of organ dysfunction in multiple organ dysfunction syndrome," Am J Emerg Med. Jul. 2008; 26 (6):711-5.

Wellmann U, et al., "The evolution of human anti-double-stranded DNA autoantibodies," Proc Natl Acad Sci USA 2005; 102:9258-63.

Zhang X., et al., "An Oligodeoxynucleotide with CCT Repeats Restrains CpG ODN-Induced TLR9 Trafficking," Curr. Pharmaceut Biotechnol. 2014; 15:780-789.

Zhang YS, et al., "Structure-activity relationship of a guanine-free oligodeoxynucleotide as immunopotent inhibitor," International Immunopathol. 2012; 13(4):446-463.

Zhang, Yongsheng "Inhibitory Effect and Structure Activity Relationship of a Human Microsatellite DNA Mimicking Oligonucleotide," Thesis Defense date: Jun. 2012.

\* cited by examiner

SEQUENCE LISTING

```
<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide: (CCT)8C

<400> SEQUENCE: 1
cctcctcctc ctcctcctcc tcctc                                          25
```

<210> SEQ ID NO 2
<211> LENGTH: 26
<212> TYPE: DNA
<213> ORGANISM: Artificial Sequence
<220> FEATURE:
<223> OTHER INFORMATION: synthetic oligonucleotide: (CCT)8CC

<400> SEQUENCE: 2
cctcctcctc ctcctcctcc tcctcc                                       26

<210> SEQ ID NO 3
<211> LENGTH: 27
<212> TYPE: DNA
<213> ORGANISM: Artificial Sequence
<220> FEATURE:
<223> OTHER INFORMATION: synthetic oligonucleotide: (CCT)9

<400> SEQUENCE: 3
cctcctcctc ctcctcctcc tcctcct                                      27

<210> SEQ ID NO 4
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 4
cctcctcctc ctcctcctcc tcctcctc                                     28

<210> SEQ ID NO 5
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 5
cctcctcctc ctcctcctcc tcctcctcc                                    29

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide: (CCT)10

<400> SEQUENCE: 6
cctcctcctc ctcctcctcc tcctcctcct                                   30

<210> SEQ ID NO 7
<211> LENGTH: 31
<212> TYPE: DNA
<213> ORGANISM: Artificial Sequence
<220> FEATURE:
<223> OTHER INFORMATION: synthetic oligonucleotide: (CCT)10C

<400> SEQUENCE: 7
cctcctcctc ctcctcctcc tcctcctcct c                                 31

<210> SEQ ID NO 8
<211> LENGTH: 32
<212> TYPE: DNA
<213> ORGANISM: Artificial Sequence
<220> FEATURE:
<223> OTHER INFORMATION: synthetic oligonucleotide: (CCT)10CC

```
<400> SEQUENCE: 8
cctcctcctc ctcctcctcc tcctcctcct cc                                32

<210> SEQ ID NO 9
<211> LENGTH: 33
<212> TYPE: DNA
<213> ORGANISM: Artificial Sequence
<220> FEATURE:
<223> OTHER INFORMATION: synthetic oligonucleotide: (CCT)11

<400> SEQUENCE: 9
cctcctcctc ctcctcctcc tcctcctcct cct                               33

<210> SEQ ID NO 10
<211> LENGTH: 34
<212> TYPE: DNA
<213> ORGANISM: Artificial Sequence
<220> FEATURE:
<223> OTHER INFORMATION: synthetic oligonucleotide: (CCT)11C

<400> SEQUENCE: 10
cctcctcctc ctcctcctcc tcctcctcct cctc                              34

<210> SEQ ID NO 11
<211> LENGTH: 35
<212> TYPE: DNA
<213> ORGANISM: Artificial Sequence
<220> FEATURE:
<223> OTHER INFORMATION: synthetic oligonucleotide: (CCT)11CC

<400> SEQUENCE: 11
cctcctcctc ctcctcctcc tcctcctcct cctcc                             35

<210> SEQ ID NO 12
<211> LENGTH: 36
<212> TYPE: DNA
<213> ORGANISM: Artificial Sequence
<220> FEATURE:
<223> OTHER INFORMATION: synthetic oligonucleotide: (CCT)12

<400> SEQUENCE: 12
cctcctcctc ctcctcctcc tcctcctcct cctcct                            36

<210> SEQ ID NO 13
<211> LENGTH: 42
<212> TYPE: DNA
<213> ORGANISM: Artificial Sequence
<220> FEATURE:
<223> OTHER INFORMATION: synthetic oligonucleotide: (CCT)14

<400> SEQUENCE: 13
cctcctcctc ctcctcctcc tcctcctcct cctcctcctc ct                     42

<210> SEQ ID NO 14
<211> LENGTH: 48
<212> TYPE: DNA
<213> ORGANISM: Artificial Sequence
<220> FEATURE:
<223> OTHER INFORMATION: synthetic oligonucleotide: (CCT)16

<400> SEQUENCE: 14
cctcctcctc ctcctcctcc tcctcctcct cctcctcctc ctcctcct               48
```

```
<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide: (CCT)6

<400> SEQUENCE: 15
cctcctcctc ctcctcct                                                    18

<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide: (CCT)7

<400> SEQUENCE: 16
cctcctcctc ctcctcctcc t                                                21

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide: CpG2395

<400> SEQUENCE: 17
tcgtcgtttt cggcgcgcgc cg                                               22

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide: CpG1826

<400> SEQUENCE: 18
tccatgacgt tcctgacgtt                                                  20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide: CpG2216

<400> SEQUENCE: 19
gggggacgat cgtcggggggg                                                 20

<210> SEQ ID NO 20
<211> LENGTH: 24
<212> TYPE: DNA
<213> ORGANISM: Artificial Sequence
<220> FEATURE:
<223> OTHER INFORMATION: synthetic oligonucleotide: (CCT)8

<400> SEQUENCE: 20
cctcctcctc ctcctcctcc tcct                                             24
```

INHIBITORY OLIGONUCLEOTIDE AND USE THEREOF

FIELD OF THE DISCLOSURE

The present invention relates to the oligonucleotides and remedies for treating immune-mediated disorders, using the oligonucleotides. The immune-mediated disorder includes autoimmune disease, graft rejection, hypersensitivity, diseases associated with the over-stimulation of host's immune system by autoantigens, microbes and Toll-like receptor (TLR)-mediated disease.

BACKGROUND ART

The immune system protects human body from bacterial, parasitic, fungal, viral infections and from the growth of tumor cells. Immunity can be classified as innate immunity or as adaptive immunity. Innate immune responses typically occur immediately upon infection for providing of an early barrier to infectious disease whereas adaptive immune responses occur later with the generation of antigen-specific long term protective immunity.

However, the immune response can sometimes be unwanted and cause immune-mediated disorder. The disorder includes autoimmune disease, graft rejection, hypersensitivity, diseases associated with the over-stimulation of host's immune system by microbes and Toll-like receptor (TLR)-mediated disease. The autoimmune diseases results from an adaptive immune response or innate immune response or both against endogenous and/or exogenous antigens. Foreign substances, derived from bacteria, parasites, fungi or viruses, may mimic self-proteins and stimulate the immune system to launch responses to a self-cell and tissue, resulting in the diseases including but not limited to systemic lupus erythematosus (SLE) and rheumatoid arthritis. The graft rejection is a consequence of organ or tissue transplantation caused by the immune response in the transplant recipient (host) to the transplanted organ/tissue. When a subject is transplanted with grafts including kidney, pancreas, heart, lung, bone marrow, cornea and skin, the subject can launch an immune response (rejection) against the grafts. Hypersensitivity is an inappropriate immune response that has deleterious effects, resulting in significant tissue damage or even death. The hypersensitivity is divided into four types (e.g. Types I, II, III and IV. Disease associated with the over-stimulation of host's immune system by microbes is triggered by the infection of viruses such as flu viruses and other microbes. In the case of flu virus and Gram-negative bacterial infection, an excessive immune response to the invaders appears to be a fatal factor in patients. The response is characterized by the overproduction of cytokines. Studies of septic shock syndrome demonstrate that over production/aberrant production of cytokines can lead to rapid mortality due to cytokine-mediated lethal shock (Slifka M K, et al. J Mol Med. 2000; 78(2): 74-80). Septic shock following gram-negative infection is a leading cause of mortality in critically ill patients. The exaggerated production of cytokines is known to contribute to sepsis characterized by cytokine-mediated lethal shock (Espat N J, et al. J Surg Res. 1995 July; 59 (1):153-8). Multiple organ dysfunction syndromes (MODS) are a major cause of morbidity and mortality in severe sepsis and shock. Cytokine-mediated lethal shock resulted from over-production of host cytokines is considered a main mechanism leading to MODS (Wang H, et al. Am J Emerg Med. 2008 July; 26 (6):711-5). Toll-like receptor (TLR)-mediated disease is a disorder caused by the activation of Toll like receptors (TLRs).

TLRs are a family of receptors that recognize microbe derived molecular structures (pathogen-associated molecular patterns or PAMPs). TLR expressing immune cells are activated upon binding of PAMPs. TLRs recognize a range of pathogen-derived products and activated. Lipopolysaccharide (LPS) of bacteria recognized by TLR4, lipotechoic acid and diacylated lipopeptides by TLR2-TLR6 dimmer, triacylated lipopeptides by TLR2-TLR1 dimmer, CpG containing oligonucleotide (CpG ODN) synthesized or derived from either viruses or bacteria by TLR9, bacterial flagellin by TLR5, zymosan by TLR2-TLR6 dimmer, F protein from respiratory syncytial virus (RSV) by TLR4, viral-derived double-stranded RNA (dsRNA) and poly I:C, a synthetic analog of dsRNA by TLR3; viral DNA by TLR9, single-stranded viral RNA (VSV and flu virus) and synthetic guanosine analogs such as imidazoquinolines and imiquimod by TLR7 and TLR8 (Foo Y. Liew, et al. Nature Reviews Immunology. Vol 5, June 2005, 446-458).

In recent years, TLR activation has been connected to the pathogenesis of some of diseases including sepsis, dilated cardiomyopathy, diabetes, experimental autoimmune encephalomyelitis, systemic lupus erythematosus, atherosclerosis, asthma, chronic obstructive pulmonary disease and organ failure (Foo Y. Liew, et al. Nature Review Immunology, Vol 5, 2005, 446-458). Activation of TLR9 by self DNA play an important role in the development of autoimmune diseases such as psoriasis (Gilliet M, et al. Nat. Rev. Immunol. 2008, 594-606), SLE (Christensen S R, et al. Immunity 2006; 25:417-28; Barrat F J, et al. J Exp Med 2005; 202:1131-9; Wellmann U, et al. Proc Natl Acad Sci USA 2005; 102:9258-63) and rheumatoid arthritis (Leadbetter E A, et al. Nature 2002; 416:603-7; Boule M W, et al. J Exp Med 2004; 199:1631-40).

It has been documented that TLR9 agonist activates both innate and adaptive immune response (Arthur M. Krieg. Nature Reviews Drug Discovery, Vol 5. June 2006, 471-484). It was documented an oligonucleotide with a nucleotide sequence of 5'-cctcctcctcctcctcctcctcct-3' prevented proliferation of human peripheral blood mononuclear cells (PBMCs) and production of IFNs, which induced by TLR9 agonists (U.S. Pat. No. 8,030,289B2).

The references cited herein are not admitted to be prior art to the claimed invention.

SUMMARY OF THE INVENTION

The present invention provides an oligonucleotide that comprises an oligonucleotide with a formula of (CCT)nCm, wherein the n is an integer from 6 to 16, the m is 0, 1, or 2; with the proviso that when n is 8, m is 1 or 2.

(SEQ ID NO: 1)
In the first embodiment, the present invention provides an oligonucleotide with a nucleotide sequence of 5'-cctcctcctcctcctcctcctc-3'.

(SEQ ID NO: 2)
In another embodiment, the present invention provides an oligonucleotide with a nucleotide sequence of 5'-cctcctcctcctcctcctcctcc-3'.

-continued (SEQ ID NO: 3)
In another embodiment, the present invention provides an oligonucleotide with a nucleotide sequence of 5'-cctcctcctcctcctcctcctcct-3'.

(SEQ ID NO: 4)
In another embodiment, the present invention provides an oligonucleotide with a nucleotide sequence of 5'-cctcctcctcctcctcctcctcctc-3'.

(SEQ ID NO: 5)
In another embodiment, the present invention provides an oligonucleotide with a nucleotide sequence of 5'-cctcctcctcctcctcctcctcctcc-3'.

(SEQ ID NO: 6)
In another embodiment, the present invention provides an oligonucleotide with a nucleotide sequence of 5'-cctcctcctcctcctcctcctcctcct-3'.

(SEQ ID NO: 7)
In another embodiment, the present invention provides an oligonucleotide with a nucleotide sequence of 5'-cctcctcctcctcctcctcctcctcctc-3'.

(SEQ ID NO: 8)
In another embodiment, the present invention provides an oligonucleotide with a nucleotide sequence of 5'-cctcctcctcctcctcctcctcctcctcc-3'.

(SEQ ID NO: 9)
In another embodiment, the present invention provides an oligonucleotide with a nucleotide sequence of 5'-cctcctcctcctcctcctcctcctcctcct-3'.

(SEQ ID NO: 10)
In another embodiment, the present invention provides an oligonucleotide with a nucleotide sequence of 5'-cctcctcctcctcctcctcctcctcctcctc-3'.

(SEQ ID NO: 11)
In another embodiment, the present invention provides an oligonucleotide with a nucleotide sequence of 5'-cctcctcctcctcctcctcctcctcctcctcc-3'.

(SEQ ID NO: 12)
In another embodiment, the present invention provides an oligonucleotide with a nucleotide sequence of 5'-cctcctcctcctcctcctcctcctcctcctcct-3'.

(SEQ ID NO: 13)
In another embodiment, the present invention provides an oligonucleotide with a nucleotide sequence of 5'-cctcctcctcctcctcctcctcctcctcctcctcct-3'.

(SEQ ID NO: 14)
In another embodiment, the present invention provides an oligonucleotide with a nucleotide sequence of 5'-cctcctcctcctcctcctcctcctcctcctcctcctcct-3'.

(SEQ ID NO: 15)
In another embodiment, the present invention provides an oligonucleotide with a nucleotide sequence of 5'-cctcctcctcctcctcct-3'.

(SEQ ID NO: 16)
In another embodiment, the present invention provides an oligonucleotide with a nucleotide sequence of 5'-cctcctcctcctcctcctcct-3'.

In another embodiment, the present invention provides a remedy for treating immune-mediated disorder using the oligonucleotides of the invention. The immune-mediated disorder includes autoimmune disease, graft rejection, hypersensitivity, diseases associated with the over-stimulation by of host's immune system by autoantigens, microbes and Toll-like receptor (TLR)-mediated disease.

In another embodiment, the present invention provides a remedy for treating immune-mediated disorder using the oligonucleotides of the invention by inhibiting the TLR activation and IFNs production induced by TLR antagonists such as DNA vims, RNA vims and the serum from SLE patients.

In another embodiment, the present invention provides a remedy for treating immune-mediated disorders using the oligonucleotides of the invention by inhibiting production of proinflammatory cytokines and by rescuing a subject from cytokine-mediated lethal shock.

In another embodiment, the present invention provides a remedy for treating immune-mediated disorders using the oligonucleotides of the invention by inhibiting NF-κB activation induced by TLR stimulation.

In another embodiment, the present invention provides a remedy for treating SLE, sepsis and multiple organ dysfunction syndromes in a subject using the oligonucleotides of the invention.

In another embodiment, the present invention provides methods of regulating an immune response in an individual, comprising administering to an individual immunostimulatory compounds in an amount sufficient to regulate an immune response in said individual Immunoregulation according to the methods of the invention may be practiced on individuals including those suffering from a disorder associated with an unwanted activation of immune response.

In another embodiment, the present invention provides methods of inhibiting a TLR9 dependent immune response in an individual, comprising administering to an individual immunostimulatory compounds in an amount sufficient to prevent TLR9 dependent cytokine production in said individual.

In another embodiment, the present invention provides methods of inhibiting a TLR7/8 dependent immune response in an individual, comprising administering to an individual immunostimulatory compounds in an amount sufficient to prevent TLR7/8 dependent cytokine production in said individual.

In another embodiment, the present invention provides methods of inhibiting a NF-κB dependent immune response in an individual, comprising administering to an individual immunostimulatory compounds in an amount sufficient to prevent NF-κB dependent cytokine production in said individual.

In another embodiment, the present invention provides a remedy for treating immune-mediated disorder by administering the oligonucleotides of the invention alone or with a pharmaceutically acceptable carrier to a subject through the route of enteral, parenteral and topical administration or inhalation.

In another embodiment, the present invention provides a composition comprising therapeutically effective amount of the oligonucleotides of the invention for the treatment of immune-mediated disorder.

In another embodiment, the present invention provides a remedy for the treatment of immune-mediated disorder by administering the oligonucleotides of the invention alone or in combination with additional active ingredients.

In the last embodiment, the present invention provides a remedy for the treatment of immune-mediated disorder by administering the oligonucleotides of the invention in delivery vehicles.

BRIEF DESCRIPTION OF DRAWINGS

(FIG. 1A) The CAL-1/NFκB-GFP cell line was designed for monitoring the activity of NF-κB transcription factor in cell-based assays. Vector encoding the GFP reporter gene driven by the NF-κB consensus transcriptional response element was transfected into human plasmacytoid DC cell line; CAL-1. GFP expression was induced by TLR9 agonist; CpG2395. (FIG. 1B) GFP expression induced by TLR9 stimulation was blocked by the addition of inhibitory-ODNs.

(FIG. 5A) Comparison of the inhibition activity between (cct)8, (cct)8c, (cct)8cc and (cct)9. (FIG. 5B) Comparison of the inhibition activity between (cct)8, (cct)9, (cct)10, (cct)11, (cct)12, (cct)14 and (cct)16.

(FIG. 7A) Comparison of the inhibition activity between (cct)6, (cct)7 and (cct)8 for NFκB activation which induced by TLR7/8 agonist; Gardiquimod. (FIG. 7B) Comparison of the inhibition activity between (cct)8, (cct)9, (cct)10, (cct)11, (cct)12, (cct)14 and (cct)16 for NF-κB activation which induced by TLR7 agonist; CL264.

DETAILED DESCRIPTION OF THE INVENTION

Figure 1A:
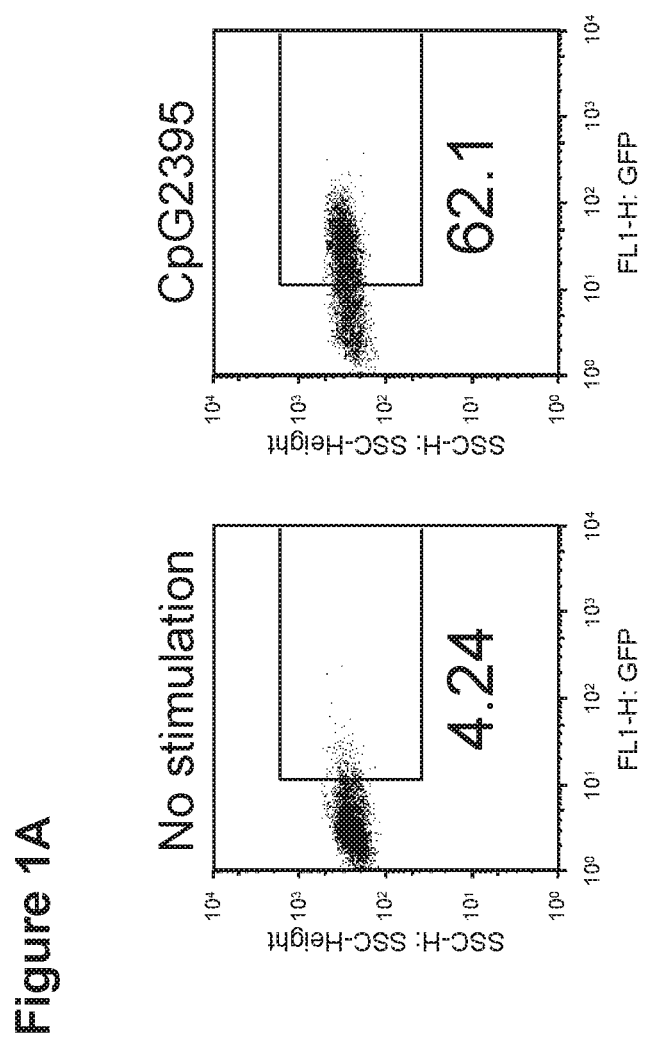
FIGS. 1A-1B show suppression of NF-κB activation by inhibitory-ODNs in human plasmacytoid DC cell line.

The oligonuleotides of the present invention strongly inhibits TLR9 activation. CpG containing oligonucleotides (CpG ODN) is known as a TLR9 agonist [D. M. Klinman, Nat. Rev., Immunol. 4 (2004) 249-258]. The oligonuleotides of the invention strongly inhibits the cytokines stimulated by CpG ODN, indicating that the oligonucleotides of the invention can be used as a remedy for the treatment of diseases related to TLR9 activation. Because TLR9 activation has been reported to contribute to the development of psoriasis (Gilliet M, et al. Nat. Rev. Immunol. 2008, 594-606), SLE (Barrat F J, et al. J Exp Med 2005; 202:1131-9; Wellmann U, et al. Proc Natl Acad Sci USA 2005; 102:9258-63; Christensen S R, et al. Immunity 2006; 25:417-28) and rheumatoid arthritis (Leadbetter E A, et al. Nature 2002; 416:603-7; Boule M W, et al. J Exp Med 2004; 199:1631-40), the oligonucleotides of the invention can be used as a remedy for the treatment of psoriasis, SLE and rheumatoid arthritis by inhibiting the TLR9 activation.

The oligonuleotides of the present invention strongly inhibits IFN production from human PBMC induced by TLR9 agonist. Because the elevated production of IFNs has been reported to contribute to the development of SLE (Barrat F J, et al. J Exp Med 2005; 202:1131-9; Wellmann U, et al. Proc Natl Acad Sci USA 2005; 102:9258-63), the oligonucleotides of the invention can be used as a remedy for the treatment of SLE by inhibiting IFN production.

The oligonuleotides of the present invention strongly inhibits the cytokines production which induced by TLR7/8 agonist. The oligonucleotides of the present invention can be used as a remedy for the treatment of Toll-like receptor (TLR)-mediated disease by inhibiting TLR7 or TLR8.

It has been demonstrated that injection of TLR9 agonist; CpG ODN with the D-galactosamine (D-Gal) into mice induced hyper immune reactions. The model mice died within 12 to 24 h. Analyses of plasma cytokines revealed over-production of proinflammatory cytokines such as TNFα (Marshall A J, et al. Infect Immun 1998 April; 66(4):1325-33; Peter M, Bode K, et al. Immunology. 2008 January; 123(1):118-28). The oligonucleotides of the present invention strongly inhibits the production of TNFα from mouse cells induced by TLR9 stimulation Because the cytokine-mediated lethal shock contributes to the septic shock (Slifka M K, et al. J Mol Med. 2000; 78(2):74-80; Espat N J, et al. J Surg Res. 1995 July; 59(1):153-8) and multiple organ dysfunction syndromes (MODS) (Wang H, et al. Am J Emerg Med. 2008 July; 26(6):711-5), the oligonucleotides of the present invention can be used as a remedy for the treatment of sepsis and MOGS by rescuing the host from cytokine-mediated lethal shock.

NF-κB is clearly one of the most important regulators of proinflammatory gene expression. Activation of the NF-κB plays a central role in inflammation through its ability to induce transcription of proinflammatory cytokines (Baldwin (Jr) A S, et al. Annu Rev Immunol. 1996, 649-683). It has been demonstrated that NF-κB plays a role in constitutive IL-6 production in rheumatoid arthritis (RA) synovial fibroblasts (Miyazawa K, et al. Am J Pathol 1998, 793-803). NF-κB is intimately involved in activation of inflammatory genes by IL-1 or TNFα in human monocytes (Schottelius A J, et al. J Biol Chem 1999, 31868-31874). The number of NF-κB positive cells correlates with the degree of gastritis. Similarly, there is evidence of NF-κB activation in inflammatory bowel disease, where lamina propria macrophages display activated NF-κB (Neurath M F, et al. Ann NY Acad Sci 1998, 859:149-159).

The activation of TLRs by the ligands induces the activation of transcription factors such as NF-κB and interferon responsive factors (IRFs). Those activated transcription factors further induce the production of cytokines such as interleukin-6 (IL-6), tumor necrosis factor alpha (TNFα) and the interferons (IFNs).

The oligonuleotides of the invention strongly inhibits NF-κB activation induced by TLR stimulation, indicating that the oligonucleotides of the invention can be used as a remedy for the treatment of diseases related to NF-κB activation. As NF-κB activation has been reported to contribute to the development of rheumatoid arthritis, gastritis and inflammatory bowel disease, the oligonucleotides of the invention can be used as a remedy for the treatment of rheumatoid arthritis, gastritis and inflammatory bowel disease by inhibiting the NF-κB activation.

Unless otherwise noted, all terms in the invention have the same meaning as commonly understood by one of ordinary skill in the art to which this disclosure belongs. The singular terms "a," "an," and "the" include plural referents unless context indicates otherwise. Similarly, the word "or" is intended to include "and" unless the context indicates otherwise. In case of conflict, the present specification, including explanations of terms, will control. In addition, the materials, methods and examples are illustrative only and not intended to be limiting. Treat, treating or treatment shall have the same meaning without concerning the grammar. Similarly, prevent, preventing or prevention shall have the same meaning without concerning the grammar. "Oligonucleotide": An oligonucleotide means multiple nucleotides (i.e. molecules comprising a sugar (e.g. deoxyribose) linked to a phosphate group and to an exchangeable organic base, which is either a substituted pyrimidine (Py) (e.g., cytosine (C), thymine (T)) or a substituted purine (Pu) (e.g., adenine (A) or guanine (G)). The term oligonucleotide as used herein refers to oligodeoxyribonucleotide (ODN). The oligonucleotide can be obtained from existing nucleic acid sources (e.g., genomic or cDNA), but are preferably synthetic. The oligonucleotide of the invention can be synthesized by a variety of automated nucleic acid synthesizers available in the market. These oligonucleotides are referred to as synthetic oligonucleotides.

"Chemical modification": The oligonucleotide disclosed in the invention can encompass various chemical modifications, in comparison to natural DNA, involving a phosphodiester internucleoside bridge, a ribose unit and/or a natural nucleoside base (adenine, guanine, cytosine, thymine). The modifications can occur either during or after synthesis of the oligonucleotide. During the synthesis, modified bases can be incorporated internally or on its end. After the synthesis, the modification can be carried out using the active groups (via an amino modifier, via the 3' or 5' hydroxyl groups, or via the phosphate group). The skilled person knows examples of chemical modifications. An oligonucleotide according to the invention may have one or more modifications, wherein each modification is located at a particular phosphodiester internucleoside bridge and/or at a particular ribose unit and/or at a particular natural nucleoside base position in comparison to an oligonucleotide of the same sequence, which is composed of natural DNA. The chemical modification includes "back bone modification" of the oligonucleotide of the invention. As used herein, the modified back bone of the oligonucleotide of the invention includes, but not limited to the "phosphorothioate backbone" that refers to a stabilized sugar phosphate backbone of a nucleic acid molecule in which a non-bridging phosphate oxygen is replaced by sulfur at least one internucleotide linkage. In one embodiment a non-bridging phosphate oxygen is replaced by sulfur at each and every internucleotide linkage Other back bone modifications denote the modification with nonionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated. In other examples, the oligonucleotide can be is a phosphorothioate/phosphodiester chimera. The chemical modification also includes the base substitutions of the oligonucleotide disclosed in the invention. The substituted purines and pyrimidines can be C-5 propyne pyrimidine and 7-deaza-7-substituted purine. The substituted purines and pyrimidines include but are not limited to adenine, cytosine, guanine, and thymine, and other naturally and non-naturally occurring nucleobases. The chemical modification of the oligonucleotide of the invention further includes the modification of the bases of the oligonucleotide. A modified base is any base which is chemically distinct from the naturally occurring bases typically found in DNA such as T, C, G and A, but which share basic chemical structures with these naturally occurring bases. The oligonucleotide of the invention can be modified by using cytidine derivatives. The term "cytidine derivative" refers to a cytidine-like nucleotide (excluding cytidine) and the term "thymidine derivative" refers to a thymidine-like nucleotide (excluding thymidine). In addition, the oligonucleotides of the invention can be chemically modified by linking a diol, such as tetraethyleneglycol or hexaethylencglycol, at either or both termini of the oligonucleotide.

"Immune-mediated disorder": An immune-mediated disorder is a disease caused by an unwanted immune response in a subject. The disorder includes autoimmune disease, graft rejection, hypersensitivity, diseases associated with the over-stimulation of host's immune system by microbes and diseases associated with TLR activation. The oligonucleotide disclosed in the invention can be used as a remedy to treat the immune-mediated disorder.

"Immune response": A response of a cells of the immune system, such as a B cell, T cell, natural killer cell, dendritic cell, neutrophil and macrophage to a stimulus. The response includes innate immune response and adaptive (specific or acquired) immune response. The adaptive (specific or acquired) immune response includes humoral immune response and cellular immune response.

"Prevent or treat immune-mediated disorder": As used herein, prevent refers to prevent the full development of an immune-mediated disorder in a subject; treat refer a therapeutic intervene in a subject so as to ameliorate a sign or symptom of, halt the progression of, or eliminate pathological condition of the immune-mediated disorder.

"Subject": As used herein, a subject refers to a human or non-human vertebrate. Non-human vertebrates are non-human primates, livestock animals and companion animals. The oligonucleotide of the invention can be administered to prevent or/and treat immune-mediated disorder in a subject.

"Autoimmune diseases": The term "autoimmune disease" refers to a disease caused by a breakdown of self-tolerance such that the adaptive and innate immune system responds to self antigens and mediates cell and tissue damage Autoimmune diseases are frequently characterized by means of their involvement of single organ or single cell-types or involvement of multiple organs or tissue systems. Autoimmune diseases have also been referred to as "collagen," or "collagen-vascular" or "connective tissue" diseases. Autoimmune disorders are frequently associated with hypersensitivity reactions. The oligonucleotides of the invention can be useful for treating and/or preventing various types of autoimmune diseases. Specific, non-limiting examples of autoimmune disorders are systemic lupus erythematosus, insulin-dependent (type I) diabetes mellitus, inflammatory arthritis, rheumatoid arthritis, multiple sclerosis, autoimmune hepatitis, chronic aggressive hepatitis, autoimmune hemolytic anemia, autoimmune thrombocytopenia, autoimmune atrophic gastritis of pernicious anemia, autoimmune encephalomyelitis, autoimmune orchitis, acquired hemophilia, ankylosing spondylitis, antiphospholipid syndrome, Beh.cedilla et's syndrome, cardiomyopathy, chronic inflammatory demyelinating polyneuropathy, cicatricial pemphigoid, cold agglutinin disease, polymyositisdermatomyositis, discoid lupus, sympathetic ophthalmia, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, systemic sclerosis, polyarteritis nodosa, polychondritis, dermatomyositis, primary agammaglobulinemia, primary biliary cirrhosis, hyperimmunoglobulin E, progressive systemic sclerosis, psoriasis, Reiter's syndrome, sarcoidosis, stiff-man syndrome, uveitis, vasculitis, vitiligo, Hashimoto's thyroiditis, Goopasture's disease, pernicious anemia, Addison's disease, dermatomyositis, Sjogren's syndrome, dermatomyositis, myasthenia gravis, Grave's disease, uveitis, allergic encephalomyelitis, glomerulonephritis, and the like (N Engl J Med, Vol. 345, No. 5, Aug. 2, 2001, p 340-350). DNA or RNA released from DNA- or RNA-containing microbes could stimulate the production of autoantibody specific to self RNA- or DNA-containing complexes and consequently led to an autoimmune disease, including but not limited to SLE.

"Hypersensitivity": A hypersensitivity is referred to the disorders wherein tissue injury occurs as a result of a humoral or cell-mediated response to antigens of endogenous or exogenous origin and has been classified into four types. Type I hypersensitivity (frequently referred to as anaphylactic, immediate-type, atopic, reagenic, IgE-mediated hypersensitivity reactions or allergy) generally result from the release of pharmacologically active substances such as histamine, slow-reacting substance of anaphylaxis (SRS-A), and eosinophilic chemotactic factor (ECF) form IgE-sensitized basophils and mast cells after contact with a specific exogenous antigen. Type I hypersensitivity includes, but not limited to, allergic extrinsic asthma, seasonal allergic rhinitis and systemic anaphylaxis. Type II hypersensitivity (also referred to as cytotoxic, cytolytic complement-dependent or cell-stimulating hypersensitivity reaction) results when antibody reacts with antigenic components of cells or tissue elements or with an antigen or hapten, which has become intimately coupled to cells or tissue. Type II hypersensitivity includes, but not limited to, autoimmune hemolytic anemia, erythroblastosis fetalis and Goodpasture's disease. Type III hypersensitivity (also referred to as toxic complex, soluble complex, or immune complex hypersensitivity reactions) results from the deposition of soluble circulating antigen-antibody complexes in vessels or in tissues, with accompanying acute inflammatory reactions at the site of immune complex deposition. Type III hypersensitivity includes, but not limited to, Arthurs reaction, serum sickness, systemic lupus erythematosis, and certain types of glomerulonephritis. Type IV hypersensitivivity (frequently called cellular, cell-mediated, delayed, or tuberculin-type hypersensitivity reactions) are caused by sensitized T-lymphocytes which result from contact with a specific antigen. Type IV hypersensitivity includes, but not limited to, contact dermatitis and allograft rejection (Richard A. et al Immunology, Fifth Edition, 2003, W.H. FREEMAN AND COMPANY).

"Diseases associated with the over-stimulation of host's immune system by microbes": Microbe invasion, if severe, sometimes can cause systemic inflammatory response in a subject, leading to diseases associated with the over-stimulation of host's immune system by microbes. The events in the development of the diseases, such as in the case of influenza A (H5N1) or bacterial infection, include the significantly elevated blood levels of TNFα, interleukin-1 (IL-1), IL-6, IL-12, interferon alpha (IFN-α), interferon beta (IFN-β), interferon gamma (IFN-γ), chemokines interferon-inducible protein 10, monocyte chemoattractant protein 1, interleukin-8, interleukin-1β, and monocyte chemoattractant protein 1. Such responses can result in cytokine-mediated lethal shock that is responsible in part for the sepsis, ARDS, and multiorgan failure observed in many patients (The Writing Committee of the World Health Organization (WHO) Consultation on Human Influenza A/H5. Avian Influenza A (H5N1) Infection in Humans N Engl J Med 2005; 353:1374-85). The significantly elevated blood level of cytokines followed microbe infection is termed by hypercytokinemia (hypercytokinaemia) or a cytokine storm. The research suggested that patients who contract bird flu or SARS may need drugs that suppress the immune response in addition to anti-viral drugs. The oligonucleotide of the invention can be used to treat and/or prevent the diseases associated with the stimulation of host's immune system by microbes in a subject. The microbes causing the diseases includes, but not limited to, viruses, bacteria, fungi, parasites and etiological agents of Spongiform encephalopathies. The virus that cause the diseases associated with the over-stimulation of host's immune system by microbes include: SARS CoV, influenza viruses, avian flu virus HIV-1, polio viruses, hepatitis A virus; enteroviruses, human Coxsackie's viruses, rhinoviruses, echoviruses, equine encephalitis viruses, rubella viruses, dengue viruses, encephalitis viruses, yellow fever viruses, corona viruses, vesicular stomatitis viruses, rabies viruses, Ebola viruses, parainfluenza viruses, mumps virus, measles virus, respiratory syncytial virus, influenza viruses, Hantan viruses, bunga viruses, phlebovimses, Nairo viruses, hemorrhagic fever viruses; reovimses, orbiviurses and rotaviruses, Hepatitis B virus, parvoviruses, papilloma viruses, polyoma viruses, adenoviruses, herpes simplex virus (HSV) 1 and HSV-2, varicella zoster virus, cytomegalovirus (CMV), herpes viruses, variola viruses, vaccinia viruses, pox viruses, African swine fever virus, the etiological agents of Spongiform encephalopathies, delta hepatitis virus, Hepatitis C virus, foot and mouth disease virus and avian flu virus. The bacteria that can cause the diseases associated with the over-stimulation of host's immune system by microbes include: *Helicobacter pyloris, Borelia burgdorferi, Legionella pneumophilia, Mycobacteria* sps (such as. *M. tuberculosis, M. avium, M. E intracellulare, M. kansaii, M. gordonae*), *Staphylococcus aureus, Neisseria gonorrhoeae, Neisseria meningitidis, Listeria monocytogenes*, Group A *Streptococcus*, Group B *Streptococcus, Streptococcus, Streptococcus faecalis, Streptococcus bovis, Streptococcus (anaerobic* sps.), *Streptococcus pneumoniae*, pathogenic *Carnpylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogeytes, Klebsiella pneumoniae, Pasteurella multocida, Bacteroides* sp., *Fusobacterium nucleatum, Streptobacillus moniliformis, Treponema palladium, Treponema pertenue, Leptospira,* and *Actinomyces israelli*. The fungi that can cause the diseases associated with the over-stimulation of host's immune system by microbes include, but not limited to, *Cryptococcus neoformans, Histoplasma capsulatum, Coccidioides immitis, Blastomyces dermatitidis, Chlamydia trachomatis, Candida albicans*. The parasites that can cause the diseases associated with the over-stimulation of host's immune system by microbes include: *Plasmodium falciparum* and *Toxoplasma gondii*.

"Graft rejection": The graft rejection is an immune-mediated disorder caused by organ or tissue transplantation, Transplantation means the transfer of transplants (grafts) from a donor to a recipient. Grafts are the living cells, tissues, or organs transplanted from a donor to a recipient. An autograft is the a graft transferred of one's own tissue from one location to another; a syngeneic graft (isograft) is a graft between identical twins; an allogeneic graft (homograft) is a graft between genetically dissimilar members of the same species; and a xenogeneic graft (heterograft) is a transplant between members of different species. When a subject is the recipient of an allogeneic graft or a xenogeneic graft, the body can produce an immune response against the donor tissue. In this situation, there is a clear need to suppress the immune response, in order to avoid rejection of the graft (Richard A. et al. Immunology, Fifth Edition, 2003, W.H. FREEMAN AND COMPANY). The oligonucleotides of the present invention are useful when administered for the prevention of the graft rejection. Examples of the grafts are heart, kidney, liver, medulla ossium, skin, cornea, lung, pancreas, intestinum tenue, limb, muscle, nervus, duodenum, small-bowel, pancreatic-islet-cell, and the like. In some case, the recipient may be an animals as defined in "subject" of the invention.

"Toll-like receptor (TLR)-mediated diseases": A Toll-like receptor (TLR)-mediated disease means an immune mediated disorder related to the activation of members of the TLR family. The disease includes, but not limited to, the diseases include but not limited to, sepsis associated with the activation of TLR4 by lipopolysaccharide (LPS), dilated cardiomyopathy associated with the activation of TLR2, 3, 4, 9, diabetes associated with the activation of TLR2,3,4,9, experimental autoimmune encephalomyelitis associated with the activation of TLR3, systemic lupus erythematosus associated with the activation of TLR9, atherosclerosis associated with the activation of TLR4, asthma associated with the activation of TLR4 by LPS, chronic obstructive pulmonary disease associated with the activation of TLR4, EAE associated with the activation of TLR4 and organ failure associated with the activation of TLR4 (Foo Y. et al. Nature Review Immunology, Vol 5, 2005, 446-458). CpG-containing DNA (a TLR9 agonist) derived from a nucleic acid-containing infectious agent could be identified from SLE serum that induces an efficient immune response dominated by IFN-α secretion that is thought to contribute the development of SLE. The oligonucleotides of the present invention can be administered for treating and/or prevent the Toll-like receptor (TLR)-mediated diseases including but not limited to SLE in a subject.

"CpG ODN": It has been documented that TLR9 agonist activates both innate and adaptive immune response (Arthur M. Krieg. Nature Reviews Drug Discovery, Vol 5. June 2006, 471-484). CpG containing oligonucleotides (CpG ODN) is a TLR9 agonist [D. M. Klinman, Nat. Rev., Immunol 4 (2004) 249-258]. Based on the functional characteristics, CpG ODNs are divided into three types (Tomoki Ito, et al. Blood, 2006, Vol 107, Num 6: 2423-2431). A-type CpG ODN activates human plasmacytoid dendritic cells (pDCs) to produce large amount of type I interferon (IFN-a/β) and strongly activates natural killer cells (NK cells). B-type CpG ODN primarily activates B cells, resulting in their proliferation and antibody secretion. C-type CpG ODN shares the activities of both A- and B-type CpG ODN. As a TLR9 agonist, CpG ODN such as CpG 2216 or CpG 2006 or CpG 2395 can be endocytosed into a cellular compartment where they are exposed to and activate TLR9. In pDC, TLR9 activation initiate a rapid innate immune response that is characterized by the secretion of pro-inflammatory cytokines [IL-6, tumor-necrosis factor-α (TNFα)], the secretion of type I interferon (IFN) and the secretion of secretion of IFN-inducible chemokines. Through both IFN-dependent and IFN-independent pathways, innate immune cells including natural killer (NK) cells, monocytes and neutrophils are secondarily activated by the pDC. B cells activated through TLR9 have a greatly increased sensitivity to antigen stimulation and efficiently differentiate into antibody-secreting cells, and therefore contributing to the adaptive immune response, especially humoral immune response. pDC activated through TLR9 secrete IFNα, which drives the migration and clustering of pDC to lymph nodes and other secondary lymphoid tissues where the pDC activates naive and memory T cells, assists the cross-presentation of soluble protein antigens to CD8+ cytotoxic T lymphocyte (CTL) and promotes strong TH1 biased cellular CD4 and CD8 T-cell responses. Based on the above mentioned findings, it is obvious that the agents that antagonize the activity of CpG ODN can be used to treat or prevent the immune-mediated disorder by inhibiting both innate and adaptive immune response.

"pharmaceutically acceptable carrier": A pharmaceutically acceptable carrier denotes one or more solid or liquid filler, diluents or encapsulating substances that are suitable for administering the oligonucleotide of the invention to a subject. The carrier can be organic, inorganic, natural or synthetic. The carrier includes any and all solutions, diluents, solvents, dispersion media, liposome, emulsions, coatings, antibacterial and anti-fungal agents, isotonic and absorption delaying agents, and any other carrier suitable for administering the oligonucleotide of the invention and their use is well known in the art. The pharmaceutically acceptable carriers are selected depending on the particular mode of administration of the oligonucleotide. The parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"therapeutically effective amount": In order to treat or prevent an immune-mediated disorder, a therapeutically effective amount of an oligonucleotide of the invention is administered to a subject. The "therapeutically effective amount" of one of the oligonucleotides means a sufficient amount of the oligonucleotide used to achieve a desired result of treating or preventing an immune-mediated disorder in a subject. The oligonucleotides of the present invention may be employed in pure form or in pharmaceutically acceptable carriers. Alternatively, the oligonucleotides may be administered as pharmaceutical compositions. The "amount" in the invention shall refer to a dose. The dose can be determined by standard techniques well known to those skilled in the art and can vary depending the factors including, but not limited to the size or/and overall health of the subject or the severity of the disease. Introduction of the oligonucleotide of the invention can be carried out as a single treatment or over a series of treatments. Subject doses of the oligonucleotide of the invention for the administration range from about 1 µg to 100 mg per administration. However, doses for the treatment of immune-mediated disorder may be used in a range of 10 to 1,000 times higher than the doses described above. The more preferable doses can be adjusted to provide the optimum therapeutic effect by those skilled in the art, for example, by the attending physician within the scope of sound medical judgment.

"Route of administration": For clinical use, the oligonucleotides of the invention can be administered alone or formulated in a pharmaceutical composition via any suitable route of administration that is effective to achieve the desired therapeutic result. The "route" of administering the oligonucleotide of the invention shall mean the enteral, parenteral and topical administration or inhalation. The enteral routes of administration of the oligonucleotide of the invention include oral, gastric, intestinal, and rectal. The parenteral route includes intravenous, intraperitoneal, intramuscular, intrathecal, subcutaneous, local injection, vaginal, topical, nasal, mucosal, and pulmonary administration. The topical route of administration of the oligonucleotide of the invention denotes the application of the oligonucleotide externally to the epidermis, to the buccal cavity and into the ear, eye and nose.

"pharmaceutical composition" A pharmaceutical composition shall mean the composition comprising an therapeutically effective amount of the oligonucleotide of the invention with or without a pharmaceutically acceptable carrier. The pharmaceutical compositions can comprise one or more oligonucleotides of the invention. The composition includes but not limited to aqueous or saline solutions, particles, aerosols, pellets, granules, powders, tablets, coated tablets, (micro) capsules, suppositories, syrups, emulsions, suspensions, creams, drops and other pharmaceutical compositions suitable for use in a variety of drug delivery systems. The compositions may be administered parenterally, orally, rectally, intravaginally, intraperitoneally, topically (in a dosage form as powders, ointments, gels, drops or transdermal patch), bucally, or as an oral or nasal spray. In all cases, the composition must be sterile and stable under the conditions of manufacture and storage and preserved against the microbial contamination. Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. The oligonucleotide of the invention can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. The buffer solution includes sodium citrate-citric acid and sodium phosphate-phosphoric acid, and sodium acetate-acetic acid buffers. For oral administration, the composition will be formulated with edible carriers to form powders tablets, pills, dragees, capsules, liquids, gels, syrups, slurries, suspensions and the like. For solid compositions, conventional non-toxic solid carriers can include pharmaceutical grades of mannitol, lactose, starch, or magnesium stearate. For buccal administration, the composition will be tablets or lozenges in conventional manner. For inhalation, the composition will be an aerosol spray from pressurized packs or a nebulizer or a dry powder and can be selected by one of skill in the art. In some cases, in order to prolong the effect of the oligonucleotide of the invention, the oligonucleotides of the invention are also suitably administered by sustained-release systems. The oligonucleotide of the invention can be used in a liquid suspension of crystalline or amorphous material with poor water solubility to slow the releasing of the oligonucleotide. Alternatively, delayed releasing of a parenterally administered drug form of the oligonucleotide is accomplished by dissolving or suspending the oligonucleotide in hydrophobic materials (such as an acceptable oil vehicle). Injectable depot forms are made by entrapping the oligonucleotide in liposomes or microemulsions or other biodegradable semipermeable polymer matrices such as polylactide-polyglycolide, poly (orthoesters) and poly (anhydrides).

"Active ingredients". The oligonucleotides of the invention can be used alone, in combination with themselves, in a pharmaceutically acceptable carrier, in combination with one or more additional active ingredients. The administration of the oligonucleotide of the invention and additional active ingredients can be sequential or simultaneous. The active ingredients include non-steroidal anti-inflammatory agents, steroids, nonspecific immunosuppressive agent, biological response modifier, chemical compound, small molecule, nucleic acid molecule and TLR antagonists. The active ingredients also denote the agents that suppress the immune activation by antagonizing chemochines, by inducing the generation of regulatory T cells (CD4+CD25+ T cells), by inhibiting a complement, matrix metalloproteases and nitric oxide synthase, by blocking costimulatory factors and by inhibiting the signaling cascades in the immune cells. The non-steroidal anti-inflammatory agents include, but unlimited to, diclofenac, diflunisal, etodolac, flurbiprofen, ibuprofen, indomethacin, ketoprofen, ketorolac, nabumetone, naproxen, oxaprozin, piroxicam, sulindac, tohnetin, celecoxib and rofecoxib. The steroids include, but unlimited to, cortisone, dexamethasone, hydrocortisone, methylprednisolone, prednisolone, prednisone, and triamcinolone. A nonspecific immunosuppressive agent means the agent used to prevent the development of immune-mediated disorder. The nonspecific immunosuppressive agents include but not limited to cyclophosphamide, cyclosporine, methotrexate, steroids, FK506, tacrolimus, mycophenolic acid and sirolimus. The biological response modifier includes a recombinant interleukin-1-receptor antagonist (Kineret or anakima), a soluble p75 TNFα receptor-IgG1 fusion protein (etanercept or Enbrel), or a monoclonal antibody against TNFα (infliximab or RemicadeX). The agents also include Interferon beta-la, interleukin-10 and TGFβ.

"delivery vehicle": The oligonucleotides of the invention can be administered in/with a delivery vehicle or in a form linked with a vehicle. The vehicle includes, but not limited to, sterol (e.g., cholesterol), cochleates, emulsomes, ISCOMs; a lipid (e.g., a cationic lipid, anionic lipid), liposomes; ethylene glycol (PEG); live bacterial vectors (e.g., Salmonella, Escherichia coli, bacillus Calmette-Gurin, Shigella, Lactobacillus), live viral vectors (e.g., Vaccinia, adenovirus, Herpes simplex), virosomes, virus-like particles, microspheres, nucleic acid vaccines, polymers (e.g., carboxymethylcellulose, chitosan), polymer rings and a targeting agent that recognizes target cell by specific receptors.

"Pegylation": Pegylation is the process of covalent attachment of poly (ethylene glycol) polymer chains to another molecule, normally a drug or therapeutic protein. Pegylation is routinely achieved by incubation of a reactive derivative of PEG with the target agent. The pegylated agent can "mask" the agent from the host's immune systems, increase the hydrodynamic size of the agent which prolongs its circulatory time. The oligonucleotides of the invention can be pegylated.

EXAMPLES

The invention will now be described in more detail in the following Examples. But the invention is not limited to these Examples. In these Examples, herein, experiments using commercially available kits and reagents were done according to attached protocols, unless otherwise stated. The skilled artisan will appreciate that the oligonucleotides of the present invention can easily be applied to treat an immune-mediated disorder. The present invention will now be demonstrated by the following non-limiting examples.

The all oligonucleotides (ODNs) used in the example were synthesized in Hokkaido System Science Co. Ltd (Sapporo, Japan). TLR9 stimulatory ODNs were CpG2395 (5'-tcgtcgttttcggcgcgcgccg-3', SEQ ID No: 17), CpG1826 (5'-tccatgacgttcctgacgtt-3', SEQ ID No: 18), CpG2216 (5'-ggggacgatcgtcggggg-3', SEQ ID No: 19). Other ODNs used in the examples were (CCT)6 (5'-cctcctcctcctcctcct-3', SEQ ID No: 15), (CCT)7 (5'-cctcctcctcctcctcctcct-3', SEQ ID No: 16), (CCT)8 (5'-cctcctcctcctcctcctcctcct-3', SEQ ID No: 20), (CCT)8C (5'-cctcctcctcctcctcctcctcctc-3', SEQ ID No: 1), (CCT)8CC (5'-cctcctcctcctcctcctcctcctcc-3', SEQ ID No: 2), (CCT)9 (5'-cctcctcctcctcctcctcctcctcct-3', SEQ ID No: 3), (CCT)10 (5'-cctcctcctcctcctcctcctcctcctcct-3' SEQ ID No: 6), (CCT)10C (5'-cctcctcctcctcctcctcctcctcctcctc-3 SEQ ID No: 7), (CCT)10CC (5'-cctcctcctcctcctcctcctcctcctcctcc-3 SEQ ID No: 8), (CCT)11 (5'-cctcctcctcctcctcctcctcctcctcctcct-3', SEQ ID No: 9), (CCT)11C (5'-cctcctcctcctcctcctcctcctcctcctcctc-3', SEQ ID No: 10), (CCT)11CC (5'-cctcctcctcctcctcctcctcctcctcctcctcc-3', SEQ ID No: 11), (CCT)12 (5'-cctcctcctcctcctcctcctcctcctcctcctcct-3' SEQ ID No: 12), (CCT)14 (5'-cctcctcctcctcctcctcctcctcctcctcctcctcctcct-3', SEQ ID No: 13) and (CCT)16 (5'-cctcctcctcctcctcctcctcctcctcctcctcctcctcctcctcct-3', SEQ ID No: 14). All reagents used to manipulate the oligonucleotides (ODNs) in the following examples were pyrogen-free.

Example 1

Figure 1B:
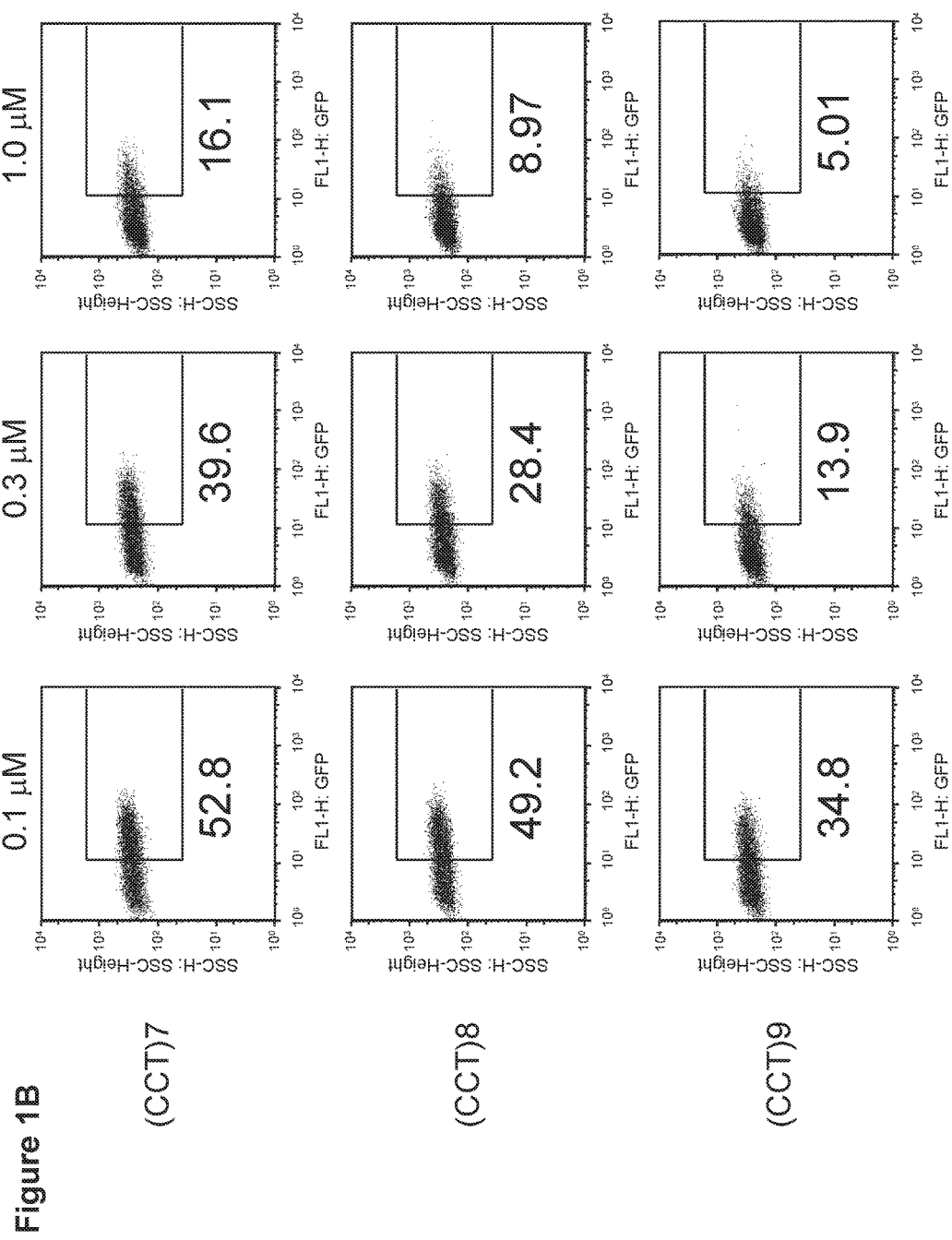

Effect of Inhibitory-ODNs on NF-κB Activation Induced by TLR9 Stimulation
<Experimental Method>
CAL-1/NFκB-GFP cell line was established for monitoring the activity of NF-κB transcription factor in cell-based assays. Vector encoding the GFP reporter gene driven by the NFκB consensus transcriptional response element was transfected into human plasmacytoid DC cell line; CAL-1 by electroporation. Transfected cells were further selected with zeocin. (FIG. 1A) GFP expression induced by TLR9 agonist; CpG2395 was evaluated. Briefly, CAL-1/NFκB-GFP cells (1×10⁵/well) were plated in 96-well flat-bottomed plate (Costar) and cultured with or without CpG2395 (1 μM). The cells were incubated at 37° C. in a 5% $CO_2$ humidified incubator for 6 hours. GFP expression level in the cells was evaluated by flow cytometer (FACS Calibur, BD Bioscience Co. Ltd). The percentage of GFP positive cells was described in the figure. (FIG. 1B) CAL-1/NFκB-GFP cells (1×10⁵/well) were pre-incubated with (CCT)7, (CCT)8 and (CCT)9 (0.1 μM, 0.3 μM, 1.0 μM) for 2 hours. The cells were stimulated with CpG2395 (1 μM) for 6 hours. GFP expression level in the cells was evaluated by flow cytometer (FACS Calibur, BD Bioscience Co. Ltd). The percentage of GFP positive cells in each condition was described in the figure.
<Experimental Result>
As shown in FIG. 1A, GFP was induced in CAL-1/NFκB-GFP cells by CpG2395 stimulation, indicating that activation of NF-κB was induced by TLR9 stimulation. Further, this GFP expression was blocked by the addition of inhibitory-ODNs. As higher concentration of inhibitory-ODNs showed better inhibition for the induction of GFP expression in CAL-1/NFκB-GFP cells, dose dependency of inhibitory activity was confirmed (maximum inhibition was observed at 1.0 μM of each inhibitory-ODN). (CCT)9 blocked GFP expression with better efficacy than that of (CCT)8 or (CCT)7. These data indicate that inhibitory-ODNs we examined can prevent NF-κB activation induced by TLR9 agonist in human cell line system.

Example 2

Figure 2A:
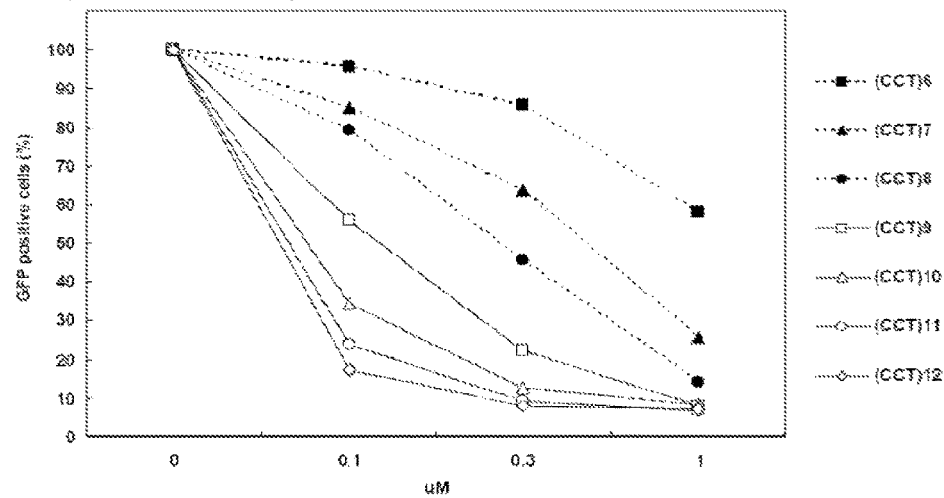
FIGS. 2A-2D show graphs depicting the suppression ability of inhibitory-ODNs on NF-κB activation by TLR9 stimulation in the CAL-1/NFκB-GFP cell line.
Figure 2B:
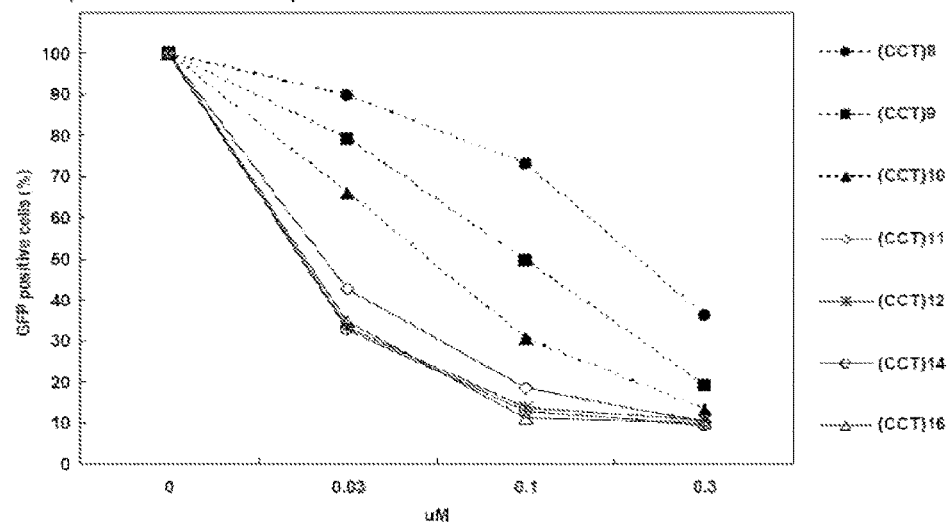

Comparison of Suppression Activity of Inhibitory-ODNs on NF-κB Activation Induced by TLR9 Stimulation
<Experimental Method>
CAL-1/NFκB-GFP cells (1×10⁵/well) were pre-incubated with various inhibitory-ODNs described above for 2 hours. The cells were stimulated with CpG2395 (1 μM) for 6 hours. GFP expression level of the cells in each condition was evaluated by flow cytometer (FACS Calibur, BD Bioscience Co. Ltd). The percentage of GFP positive cells with CpG2395 alone was defined as 100% in the graph. The percentage of GFP positive in each condition was calculated from the number.
<Experimental Result>
As shown in FIG. 2A, dose dependency of the inhibitory activity for NF-κB activation was confirmed in each inhibitory-ODN. (CCT)8 inhibited GFP expression induced by CpG2395 and showed better activity than (CCT)6 and (CCT)7 in human pDC cell line. (CCT)9 strongly blocked GFP expression with better efficacy than (CCT)8. (CCT)10, (CCT)11 and (CCT)12 exhibited much better inhibitory activity than (CCT)9. These results suggest that longer ODNs have better activity than shorter ODNs. However, The inhibitory activity of (CCT)14 and (CCT)16 was as same as the activity of (CCT)12 (FIG. 2B), suggesting that (CCT)12 as well as (CCT)14 and (CCT)16 may have maximum efficacy for the inhibition of NF-κB activity, which induced by TLR9 stimulation. Importantly, the inhibitory activity of (CCT)8 at 1.0 μM was almost same as those of (CCT)11 and (CCT)12 at 0.1 μM. This data indicate that (CCT)11 and (CCT)12 have ten times higher efficacy for the inhibition of NF-κB activation than (CCT)8 in human cells.

Figure 2C:
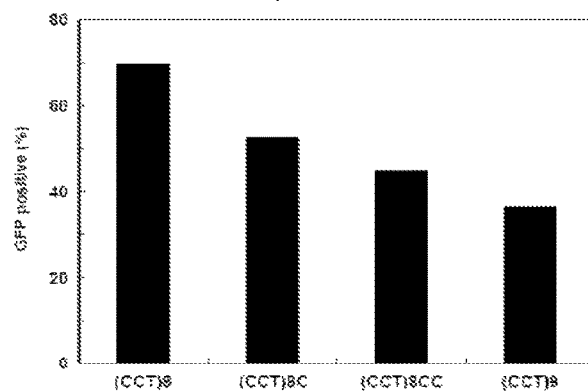
Figure 2D:
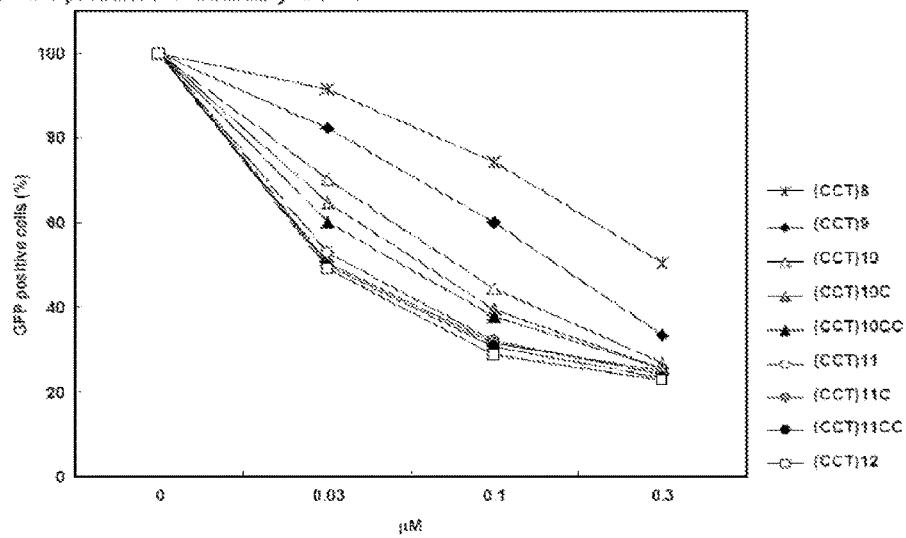

As shown in FIGS. 2C and 2D, (CCT)8C and (CCT)8CC exhibited better inhibitory activity than (CCT)8. It was also demonstrated that (CCT)10C and (CCT)10CC exhibited better inhibitory activity than (CCT)10. Further, (CCT)11C and (CCT)11CC had better inhibitory activity than (CCT)11, while the inhibitory activity of (CCT)11 was already almost saturated. These results indicated that the addition of C or CC at the 3' end of (CCT) repeats increased the inhibitory activity of the ODNs.

It is well established activated NF-κB further induce the production of proinflammatory cytokines such as interleukin-6 (IL-6) and tumor necrosis factor alpha (TNFα). As oligonuleotides (ODNs) we examined strongly inhibits NF-κB activation induced by TLR stimulation, the ODNs can be used as a remedy for the treatment of diseases related to NF-κB activation. As NF-κB activation has been reported to contribute to the development of autoimmune diseases such as rheumatoid arthritis, gastritis and inflammatory bowel disease, the ODNs we examined can be used as a remedy for the treatment of the diseases by inhibiting the NF-κB activation.

Example 3

Comparison of Suppression Activity of Inhibitory-ODNs on Proinflammatory Cytokines Production Induced by TLR9 Stimulation for Human Cells <Experimental Method>

Human plasmacytoid DC cell line; CAL-1 cells were cultured ($1 \times 10^5$/well) were plated in 96-well flat-bottomed plate (Costar) and stimulated with CpG2395 (0.4 μM) in the presence of inhibitory-ODNs for 24 hours (concentrations of the inhibitory-ODNs are described in the figure). After 24 hours stimulation, cultured supernatants were recovered and proinflammatory cytokines production was evaluated. The level of IL-6 and TNFα production were measured by ELISA as described in manufacture's protocol (R&D systems Co. Ltd, Minneapolis, USA).

<Experimental Result>

Figure 3:
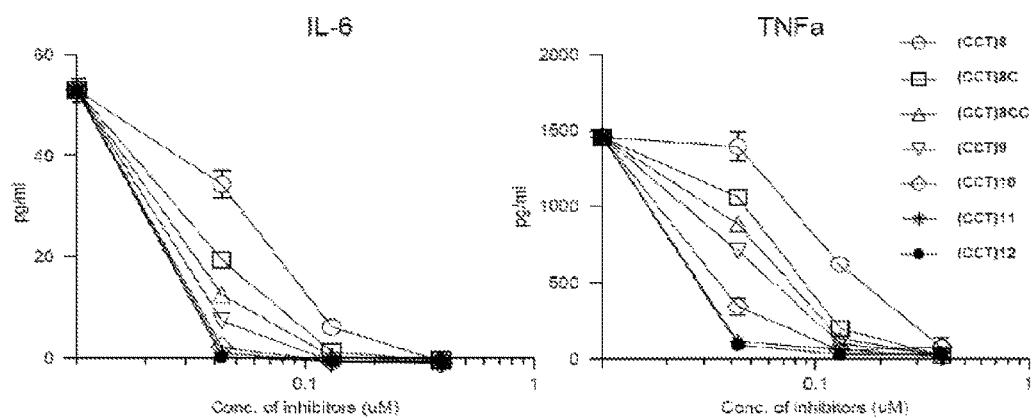
FIG. 3 shows graphs depicting the suppression ability of inhibitory-ODNs on IL-6 and TNFα production from CAL-1 cells stimulated with TLR9 agonist; CpG2395. Comparison of the inhibition activity between (cct)8, (cct)8c, (cct)8cc, (cct)9, (cct)10, (cct)11 and (cct)12.
Figure 4:
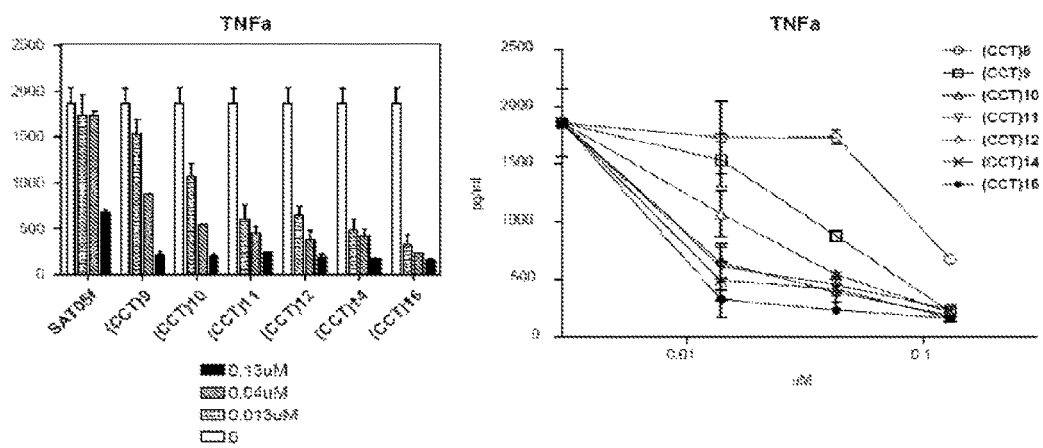
FIG. 4 shows graphs depicting the suppression ability of inhibitory-ODNs on IL-6 and TNFα production from CAL-1 cells stimulated with TLR9 agonist; CpG2395. Comparison of the inhibition activity between (cct)8, (cct)9, (cct)10, (cct)11, (cct)12, (cct)14 and (cct)16.

As shown in FIG. 3, both IL-6 and TNFα production induced by CpG2395 was blocked by the addition of inhibitory-ODNs in CAL-1 cells. Dose dependency of the inhibitory activity for IL-6 and TNFα production was confirmed in each inhibitory-ODN. (CCT)9, (CCT)10, (CCT)11 and (CCT)12 strongly blocked both IL-6 and TNFα production induced by CpG2395. The efficacy of these ODNs was much better than that of (CCT)8. Importantly, the inhibitory activity of (CCT)8 at 0.4 μM was almost same as those of (CCT)11 and (CCT)12 at 0.04 μM. This data indicates that (CCT)11 and (CCT)12 have ten times higher efficacy than (CCT)8 in human cells. As (CCT)11 and (CCT)12 exhibited almost 100% inhibition at 0.04 uM, we further evaluated the inhibitory activity at lower concentrations (FIG. 4). As shown in the figure, (CCT)9 and (CCT)10 blocked TNFα production with much better efficacy than (CCT)8. Further, (CCT)11, (CCT)12, (CCT)14 and (CCT)16 exhibited strong efficacy for the inhibition of TNFα production at very low dose in human cells. These results suggest that the ODNs can be used as a remedy for the treatment of various immune-mediated disorders such as autoimmune diseases, graft rejection, hypersensitivity, diseases associated with the over-stimulation by of host's immune system by autoantigens and microbes. As it has been reported that IL-6 and TNFα play key roles for the development of the diseases such as rheumatoid arthritis, gastritis and inflammatory bowel disease, the ODNs we examined can be used a remedy for the treatment of the diseases by the inhibition of IL-6 and TNFα.

Example 4

Comparison of Suppression Activity of Inhibitory-ODNs on Proinflammatory Cytokines Production Induced by TLR9 Stimulation for Mouse Cells <Experimental Method>

Mouse DC cell line; D2SC/1 cells were cultured D2SC/1 ($1 \times 10^5$/well) were plated in 96-well flat-bottomed plate (Costar) and stimulated with CpG1826 (0.65 μM) in the presence of inhibitory-ODNs for 24 hours (concentrations of the inhibitory-ODNs are described in the figure). After 24 hours stimulation, cultured supernatants were recovered and proinflammatory cytokines production was evaluated. The level of IL-6 and TNFα production were measured by ELISA as described in manufacture's protocol (R&D systems Co. Ltd, Minneapolis, USA).

<Experimental Result>

Figure 5A:
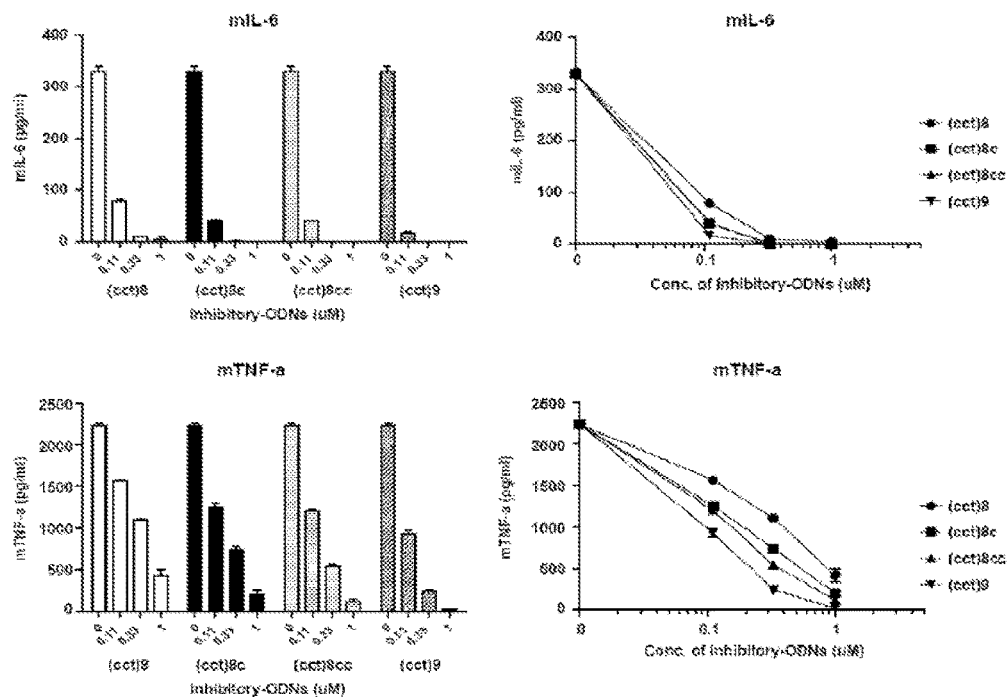
FIGS. 5A-5B show graphs depicting the suppression ability of inhibitory-ODNs on IL-6 and TNFα production from mouse DC cell line; D2SC/1. D2SC/1 cells were stimulated with TLR9 agonist; CpG1826 in the presence of inhibitory-ODNs.
Figure 5B:
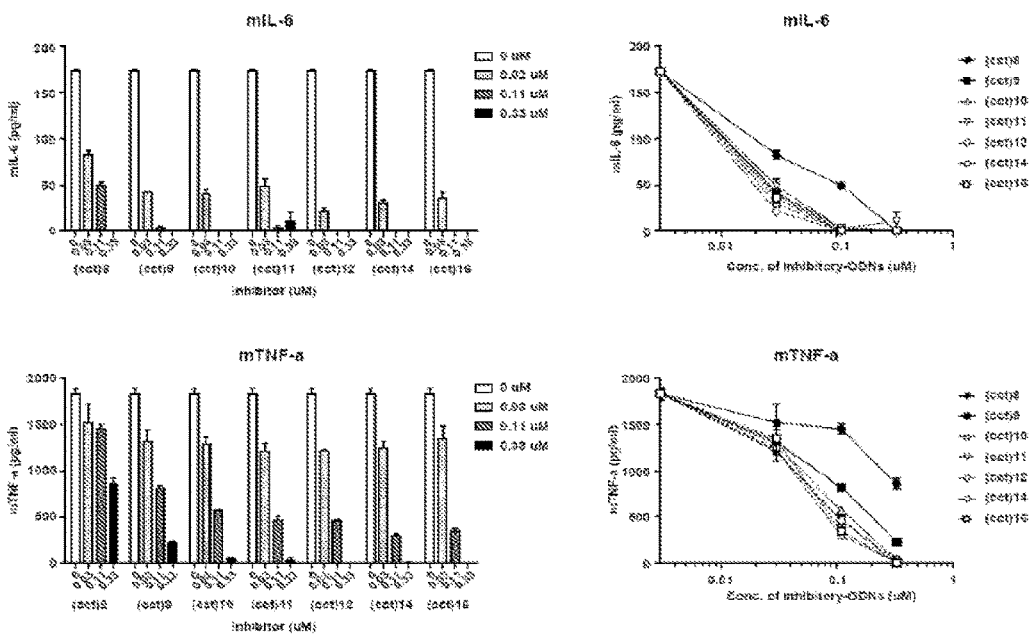

As shown in FIG. 5A, both IL-6 and TNFα production induced by CpG1826 was blocked by the addition of inhibitory-ODNs in mouse DC cell line; D2SC/1 cells. Dose dependency of the inhibitory activity for IL-6 and TNFα production was confirmed in each inhibitory-ODN. (CCT)9, (CCT)10, (CCT)11, (CCT)12, (CCT)14 and (CCT)16 strongly blocked both IL-6 and TNFα production induced by CpG1826. Importantly, the efficacy of these ODNs was much better than that of (CCT)8. As shown in FIG. 5B, (CCT)8 at 0.1 μM barely inhibited TNFα production which induced by CpG1826. However, (CCT)10, (CCT)11, (CCT)12, (CCT)14 and (CCT)16 at same concentration strongly inhibited TNFα production. This data indicates that (CCT)10, (CCT)11, (CCT)12, (CCT)14 and (CCT)16 have much better inhibitory effects than (CCT)8 for TLR9 stimulation in mouse cells.

It was documented that D-galactosamin presensitized mice with CpG ODN developed cytokine-mediated lethal shock because of the induction of hyper immune reactions (Peter M, et al. Immunology. 2008 January; 123(1):118-28). Analyses of plasma cytokines revealed over-production of proinflammatory cytokines such as TNFα (Marshall A J, et al. Infect Immun 1998 April; 66(4):1325-33; Peter M, Bode K, et al. Immunology. 2008 January; 123(1):118-28). The ODNs we evaluated strongly inhibits the production of TNF from mouse cells induced by TLR9 stimulation. Because the cytokine-mediated lethal shock contributes to the septic shock (Slifka M K, et al. J Mol Med. 2000; 78(2):74-80; Espat N J, et al. J Surg Res. 1995 July; 59(1):153-8) and multiple organ dysfunction syndromes (MODS) (Wang H, et al. Am J Emerg Med. 2008 July; 26(6):711-5), the ODNs we evaluated can be used as a remedy for the treatment of sepsis and MOGS by rescuing the host from cytokine-mediated lethal shock.

Example 5

The Suppression Activity of Inhibitory-ODNs on IFNα Production from Human PBMCs Stimulated with TLR9 Agonist.

<Experimental Method>

Human peripheral mononuclear cells (huPBMCs), used in the following samples, were isolated from peripheral blood by Ficoll-Hypaque (Pharmacia) density gradient centrifugation (P. M. Daftarian et al., (1996): Journal of Immunology, 157, 12-20). The cells were cultured in RPMI supplemented with 10% FCS (v/v) and antibiotics (100 IU of penicillin/ml and 100 IU of streptomycin/ml) at 37° C. in a 5% $CO_2$ humidified incubator. IFNα production from PBMCs induced by TLR9 stimulation was evaluated. Briefly, huPBMCs ($5\times10^6$/ml) were plated into 96 well flat-bottomed plate and stimulated with CpG2216 (1 μM) in the presence of inhibitory-ODNs (0.1 μM); (CCT)8, (CCT)9, (CCT)10, (CCT)11, (CCT)12, (CCT)14 and (CCT)16. The culture supernatants were collected for measuring the level of IFNα production. The level of IFNα production was measured by ELISA as described in manufacture's protocol (R&D systems Co. Ltd, Minneapolis, USA).

<Experimental Results>

Figure 6:
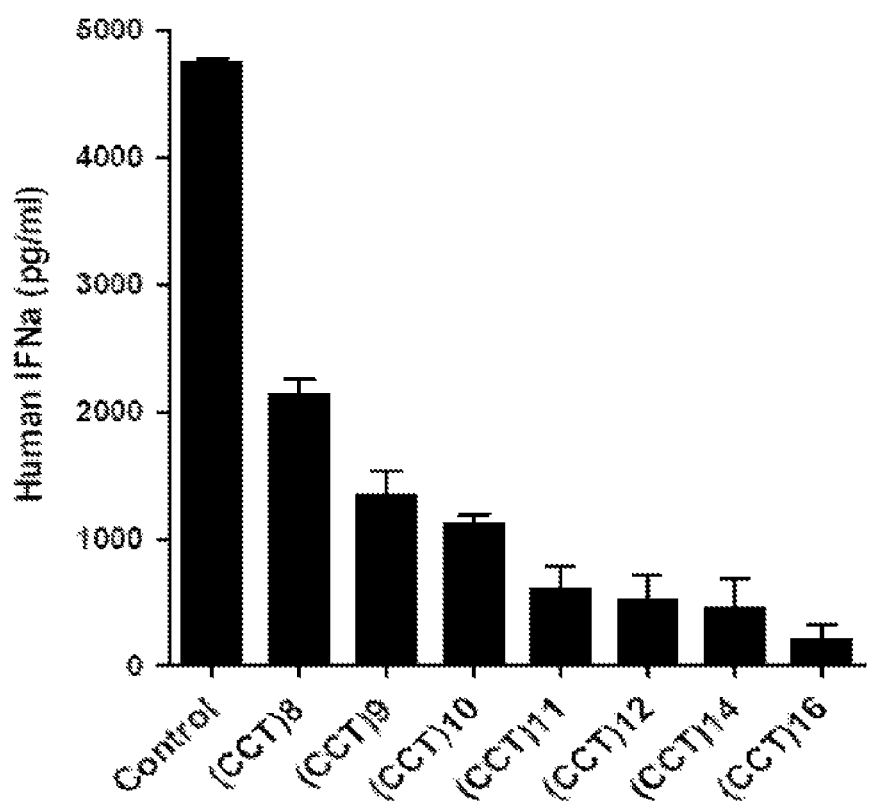
FIG. 6 shows a graph depicting the suppression activity of inhibitory-ODNs on IFNα production from human PBMC stimulated with CpG2216. Comparison of the inhibition activity between (cct)8, (cct)9, (cct)10, (cct)11, (cct)12, (cct)14 and (cct)16 on IFNα production which induced by TLR9 agonist; CpG2216.

As shown in FIG. 6, huPBMCs produced IFNα in response to TLR9 agonist; CpG2216. (CCT)8 blocked IFNα production induced by CpG2216. However, the suppression efficacy of (CCT)8 was not so strong. (CCT)9, (CCT)10, (CCT)11, (CCT)12, (CCT)14 and (CCT)16 exhibited better inhibitory activity for IFNα production by CpG2216 than (CCT)8. Especially, (CCT)11, (CCT)12, (CCT)14 and (CCT)16 strongly inhibited IFNα production induced by CpG2216. These results indicate that the inhibitory-ODNs we evaluated can be inhibitor of TLR9 and IFNα production in human PBMCs. It is well established that elevated production of IFNs contributes to the development of SLE (Barrat F J, et al. J Exp Med 2005; 202:1131-9; Wellmann U, et al. Proc Natl Acad Sci USA 2005; 102:9258-63). It has been demonstrated that endogenous IFN inducing factors has been reported existed in the serum of SLE patient (Kwok S K, et al. Arthritis Res Ther. 2008; 10(2):R29), SLE patients have a circulating inducer of IFN production, sera from SLE patient frequently induce the production of IFN via TLR9 in cultures of PBMC from healthy blood donors. As the ODNs we examined could efficiently block IFNα production, the ODNs we evaluated can be used as a remedy for the treatment of SLE patients by inhibiting IFN production.

Example 6

Comparison of Suppression Activity of Inhibitory-ODNs on NF-κB Activation Induced by TLR7/8 Stimulation <Experimental Method>

CAL-1/NFκB-GFP cells ($1\times10^5$/well) were pre-incubated for 2 hours with inhibitory-ODNs described previously. The cells were stimulated with TLR7/8 agonist; Gardiquimod or CL264 (Invivogen, USA), for 4 hours. GFP expression level of the cells in each condition was evaluated by flow cytometer (FACS Calibur, BD Bioscience Co. Ltd). FIG. 7 (A) CAL-1/NFκB-GFP cells were stimulated with TLR7/8 agonist; Gardiquimod (2 μg/ml) for 4 hours in the presence of (CCT)6, (CCT)7 and (CCT)8 (0.1 uM, 0.3 uM and 1.0 uM). The percentage of GFP positive cells with Gardiquimod alone was defined as 100% in the graph. The percentage of GFP positive in each condition was calculated from the number. FIG. 7 (B) CAL-1/NFκB-GFP cells were stimulated with TLR7/8 agonist; CL264 (1 μg/ml) for 4 hours in the presence of (CCT)8, (CCT)9, (CCT)10, (CCT)11, (CCT)12, (CCT)14 and (CCT)16 (0.01 uM, 0.03 uM and 0.1 uM). The percentage of GFP positive in each condition was calculated as described previously.

<Experimental Results>

Figure 7A:
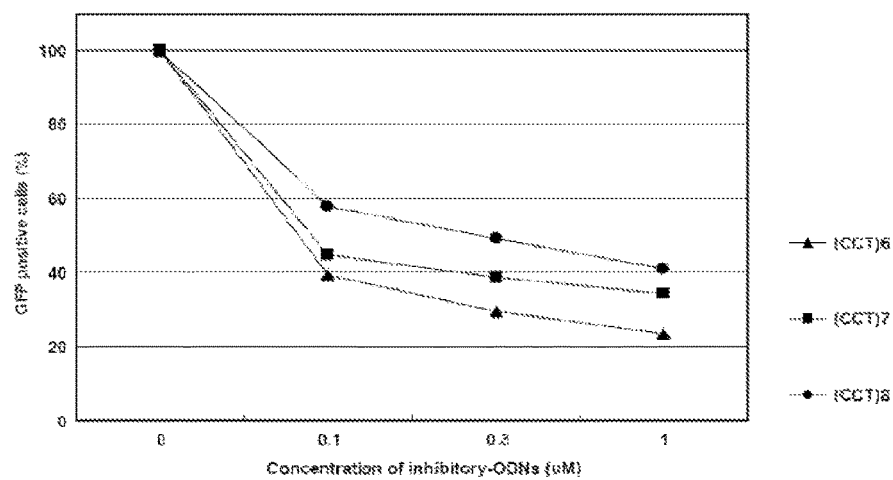
FIGS. 7A-7B show graphs depicting the suppression ability of inhibitory-ODNs on NF-κB activation by TLR7/8 stimulation in the CAL-1/NFκB-GFP cell line.
Figure 7B:
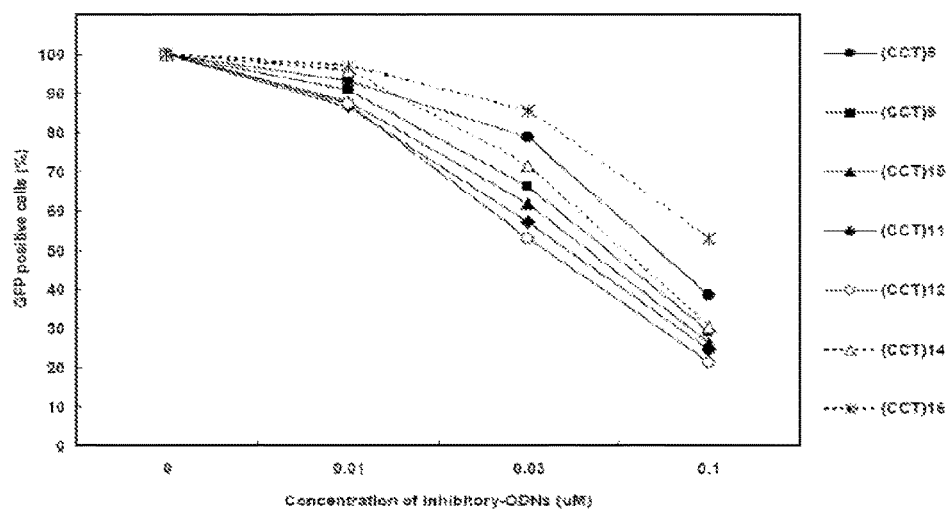

As shown in FIG. 7A, GFP expression was induced in CAL-1/NFκB-GFP cells by Gardiquimod stimulation, indicating that activation of NF-κB was induced by TLR7 stimulation. Further, this GFP expression was blocked by the addition of inhibitory-ODNs. Dose dependency of the inhibitory activity for NF-κB activation by TLR7 stimulation was confirmed in each inhibitory-ODN. (CCT)6 and (CCT)7 showed better activity for Gardiquimod stimulation than (CCT)8, while (CCT)8 also blocked GFP expression. Importantly, the inhibitory activity of (CCT)8 at 1.0 μM was almost same as those of (CCT)6 and (CCT)7 at 0.1 μM. This data indicates that (CCT)6 and (CCT)7 have ten times higher efficacy for the inhibition of NF-κB activation, which induced by TLR7 stimulation, than (CCT)8. As shown FIG. 2, (CCT)8 showed better inhibitory activity for TLR9 stimulation than (CCT)6 and (CCT)7. Thus, this suggests (CCT)6 and (CCT)7 have unique inhibitory activity for TLR7, but not TLR9, stimulation. As shown FIG. 7B, GFP expression was induced in CAL-1/NFκB-GFP cells by CL264 stimulation and this GFP expression was blocked by the addition of inhibitory-ODNs. (CCT)9 (CCT)10, (CCT)11 and (CCT)12 efficiently blocked GFP expression by CL264 stimulation and exhibited better inhibitory activity than (CCT)8. These results suggest that longer ODNs have better inhibitory activity for TLR7 stimulation, however the inhibitory activity of (CCT)14 and (CCT)16 for TLR7 stimulation was much worse than the activity of (CCT)12. This indicates that (CCT)12 may have maximum efficacy for the inhibition of NF-κB activity, which induced by TLR7 stimulation. Our data provide the ODNs we examined can block TLR7 stimulation in human cells. It has been demonstrated that uncontrolled IFN production contributes to the development of SLE (Barrat F J, et al. J Exp Med 2005; 202:1131-9; Wellmann U, et al. Proc Natl Acad Sci USA 2005; 102: 9258-63) and IFN production from huPBMCs was produced by TLR7 stimulation. Together with the results of the example, the ODNs we examined can be used as a remedy for the treatment of TLR-mediated disease such as SLE by inhibiting TLR7 or TLR9 activation.

Other embodiments are within the following claims. While several embodiments have been shown and described, various modifications may be made without departing from the spirit and scope of the present invention.

What is claimed is:

1. A method of treating an immune-mediated disorder in a human subject in need thereof, comprising administering to the human subject an oligonucleotide consisting of a sequence selected from the group consisting of:

```
                                          (SEQ ID NO: 15)
5'-cctcctcctcctcctcct-3',
and
                                          (SEQ ID NO: 16)
5'-cctcctcctcctcctcctcct-3'.
```

2. The method of claim 1, wherein the immune-mediated disorder is an autoimmune disease, hypersensitivity, graft rejection, a disease associated with over-stimulation of host's immune system by microbes, an NF-kB mediated disease or a Toll-like receptor (TLR)-mediated disease.

3. The method of claim 1, wherein the immune-mediated disorder is a TLR-mediated disease and the oligonucleotide inhibits the proliferation of immune cells.

4. The method of claim 1, wherein the immune-mediated disorder is a TLR-mediated disease and the oligonucleotide inhibits the activation of TLR7 and/or TLR8.

5. The method of claim 1, wherein the immune-mediated disorder is a NF-kB-mediated disease and the oligonucleotide inhibits the activation of NF-kB.

6. The method of claim 1, wherein the oligonucleotide inhibits interferon production.

7. The method of claim 1, wherein the oligonucleotide inhibits proinflammatory cytokine production.

8. The method of claim 1, wherein the oligonucleotide rescues the subject from cytokine-mediated lethal shock.

9. The method of claim 1, wherein the immune-mediated disorder is systemic lupus erythematosus (SLE).

10. The method of claim 1, wherein the immune-mediated disorder is rheumatoid arthritis, gastritis, or inflammatory bowel disease.

11. The method of claim 1, wherein the immune-mediated disorder is sepsis or multiple organ dysfunction syndrome.

12. The method of claim 1, wherein the oligonucleotide is administered alone or with a pharmaceutically acceptable carrier to a subject having or at risk of developing the immune-mediated disorder.

13. The method of claim 1, wherein the oligonucleotide is administered to the subject via enteral, parenteral and topical administration or inhalation.

14. The method of claim 1, wherein the oligonucleotide is administered to the subject in a pharmaceutical composition.

15. The method of claim 1, wherein the oligonucleotide is pegylated.

16. The method of claim 1, wherein the phosphate backbone of the oligonucleotide is partly or completely phosphorothioate-modified.

17. The method of claim 1, wherein the phosphate backbone of the oligonucleotide is unmodified.

18. A method of treating an immune-mediated disorder in a human subject in need thereof, comprising administering to the human subject an oligonucleotide consisting of a sequence selected from the group consisting of:
- 5'-cctcctcctcctcctcct-3' (SEQ ID NO:15), with the exception that a nucleotide is added to, deleted from, or added to and deleted from either end of the sequence, and
- 5'-cctcctcctcctcctcctcct-3' (SEQ ID NO:16), with the exception that a nucleotide is added to, deleted from, or added to and deleted from either end of the sequence.

* * * * *